(12) United States Patent
Lewis

(10) Patent No.: US 9,157,868 B2
(45) Date of Patent: Oct. 13, 2015

(54) SYSTEM AND METHOD FOR REVIEWING A CURVED SAMPLE EDGE

(71) Applicant: KLA-Tencor Corporation, Milpitas, CA (US)

(72) Inventor: Isabella T. Lewis, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 110 days.

(21) Appl. No.: 13/788,756

(22) Filed: Mar. 7, 2013

(65) Prior Publication Data

US 2014/0253910 A1    Sep. 11, 2014

(51) Int. Cl.
*G01N 21/00*    (2006.01)
*G01N 21/95*    (2006.01)

(52) U.S. Cl.
CPC .................................. *G01N 21/9503* (2013.01)

(58) Field of Classification Search
USPC .......... 356/237.1–237.5, 239.1–239.3, 239.7, 356/239.8; 382/145, 149; 257/E21.53
See application file for complete search history.

(56) References Cited

U.S. PATENT DOCUMENTS

| | | | |
|---|---|---|---|
| 7,280,197 B1 | 10/2007 | Rosengaus | |
| 7,920,254 B2 * | 4/2011 | Mysore et al. | 356/138 |
| 2006/0007435 A1 | 1/2006 | Biellak et al. | |
| 2008/0030731 A1 | 2/2008 | Jin et al. | |
| 2009/0059236 A1 * | 3/2009 | Meeks et al. | 356/445 |
| 2012/0281875 A1 | 11/2012 | Yasuda et al. | |
| 2012/0307236 A1 * | 12/2012 | Ortner et al. | 356/239.3 |

* cited by examiner

*Primary Examiner* — Tri T Ton
(74) *Attorney, Agent, or Firm* — Suiter Swantz pc llo

(57) ABSTRACT

The disclosure is directed to a system and method for reviewing a curved edge of a sample. A line scan detector is actuated along an actuation path defined by the edge of the sample to scan a plurality of locations along the sample edge. The scan data is assembled to generate at least one review image of at least a portion of the edge of the sample. In some embodiments a substantially normal angle of incidence is maintained between the sample edge and the scanning illumination. In some embodiments, brightfield and darkfield images may be collected utilizing a common objective with separately operable illumination sources directing illumination along a first and second illumination path to the sample edge for review.

31 Claims, 4 Drawing Sheets

SYSTEM AND METHOD FOR REVIEWING A CURVED SAMPLE EDGE

TECHNICAL FIELD

The present disclosure generally relates to field of sample review and more particularly to reviewing a curved edge of a sample.

BACKGROUND

Several methods exist in the art for reviewing a curved edge of a sample, such as a semiconductor wafer. For example, some wafer edge review systems collect a 2-D format image at a small angle off normal to the wafer with illumination at the reflected angle covering a radial zone of possible local wafer surface normal angles. Some other systems include a 2-D camera viewing normal to the wafer edge. In another class of systems a TDI camera with a center pixel normal to the local wafer edge is configured to image the wafer spinning on a radial stage. All of the foregoing systems, however, suffer from a limited depth of focus and/or severe image shading resulting from angle of incidence between illumination and the wafer edge. The depth of focus and shading may limit the usable field of view to very small strips.

SUMMARY

The disclosure is directed to systems and methods that cure deficiencies of the current art to enable collection of high resolution review images over the sample edge. In some embodiments, the systems and methods described below may further extended to applications beyond review imaging such as, but not limited to, inspection over the wafer edge or film review or inspection at a selected angle of incidence in radial slice planes.

In one aspect, the disclosure is directed to a system for reviewing a curved edge of a sample while avoiding field depth of focus problems by line scanning along the wafer edge. The system includes a stage configured to support a sample and at least one illumination source configured to illuminate an edge of the sample with illumination emanating along an illumination path defined by one or more illumination optics. A line scan detector is configured to receive illumination reflected from the edge of the sample along a collection path defined by one or more collection optics. At least one actuator is configured to actuate the line scan detector and the one or more collection optics radially along an actuation path defined by the edge of the sample to scan along the sample edge. A computing system communicatively coupled to the line scan detector is configured to generate at least one review image of at least a portion of the sample edge by assembling line scans associated with illumination received by the line scan detector from a plurality of locations along the edge of the sample.

In another aspect, the disclosure is directed to a system including a first illumination source configured to illuminate an edge of the sample with illumination emanating along a first illumination path and a second illumination source configured to illuminate the edge of the sample with illumination emanating a second illumination path. In some embodiments, the system further includes a beam splitter configured to merge the first illumination path and the second illumination path into a common path leading to the sample edge. The first and second illumination sources may be configured for separately operating to respectively provide for brightfield and darkfield imaging of the sample edge. In some embodiments, a common objective is configured to collect illumination reflected from the sample edge for either type of imaging.

In yet another aspect, the disclosure is directed to a method of reviewing a curved sample edge in accordance with the foregoing systems. The method may include at least the steps of: illuminating an edge of a sample with illumination emanating from a first illumination source along a first illumination path including one or more illumination optics; receiving illumination reflected from the edge of the sample along a collection path including one or more collection optics utilizing a line scan detector; actuating the line scan detector and the one or more collection optics radially along an actuation path defined by the edge of the sample; and generating at least one review image of at least a portion of the edge of the sample utilizing scan data associated with illumination received by the line scan detector from a plurality of locations along the edge of the sample.

In yet another aspect, review images on the top or bottom section of the sample, which are not curved, may be collected utilizing a two dimensional (2-D) sensor (as opposed to the line scan imager). In some embodiments, the line scan function may be achieved utilizing a windowed readout of a 2-D sensor with a minimal number of lines (i.e. on the order of 8 lines). This would allow a 2-D sensor to be in place for rapid imaging of the top and bottom flat wafer sections, and allow fast pseudo line scanning over the edge of the wafer.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

FIGS. 1 through 4 generally illustrate a system 100 and method 200 for collecting review images along curved edge 102 of a sample 101, such as a wafer, by line scanning over the sample edge 102. Line scanning over the edge of the wafer may allow for improvements in of the required depth of field, the required cone angle of bright field illumination, and thus increase the usable field of view as compared to previously known systems and methods in the art. Accordingly review images may be collected with reduced image shading due to a reduction in the depth of field and illumination limitations common to existing wafer edge review systems. Furthermore, an enhanced field of view may enable review of certain defects of interest, such as edge chips, on a relatively small scale (e.g. order of a millimeter).

Figure 1:
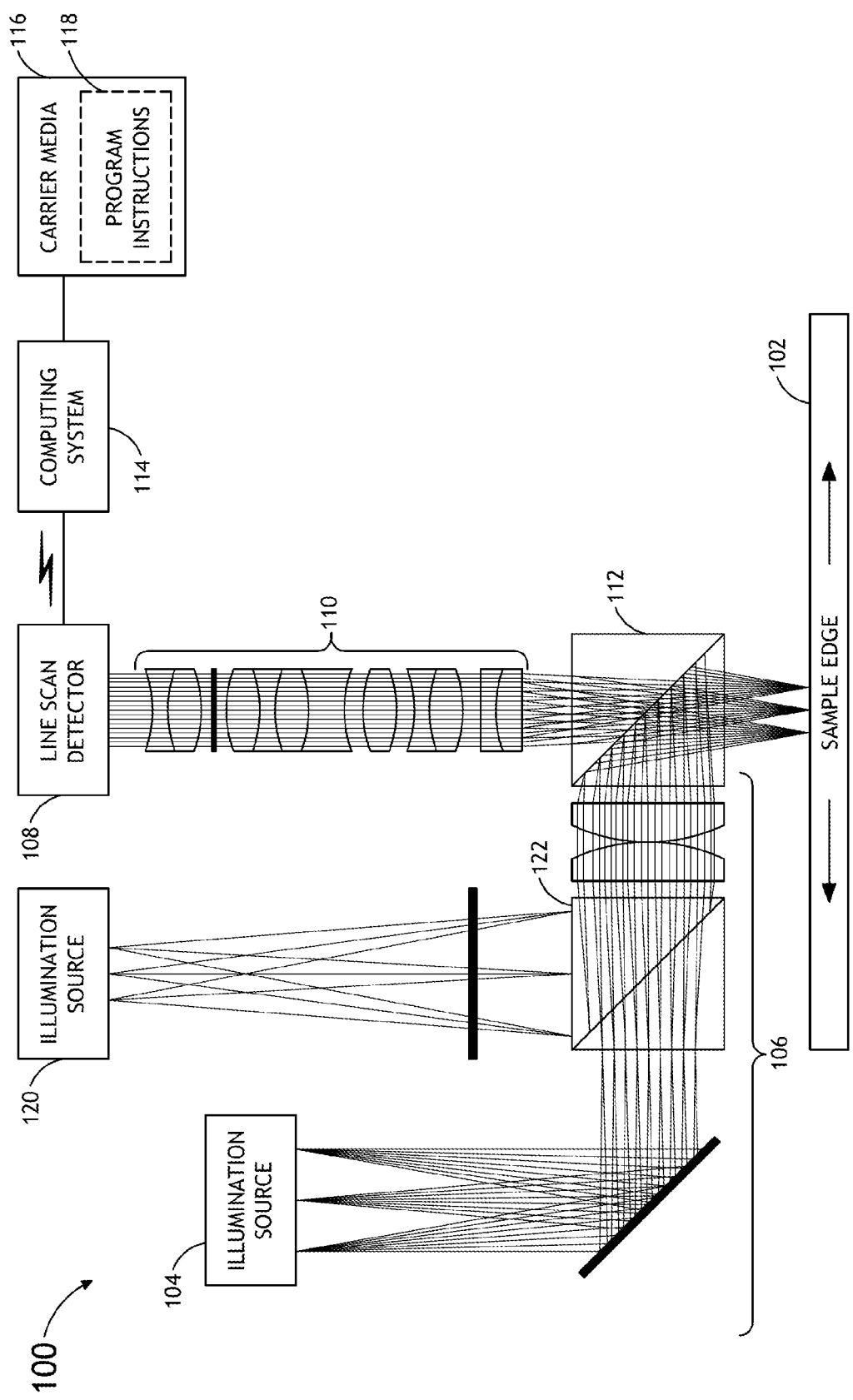
FIG. 1 is a block diagram illustrating a system for reviewing an edge of a sample, in accordance with an embodiment of this disclosure.

FIG. 1 illustrates a system 100 for reviewing an edge 102 of a sample 101, in accordance with an embodiment of the disclosure. The system 100 includes at least one illumination source 104 configured to illuminate the sample edge 102 by providing illumination along an illumination path defined by one or more illumination optics 106. The sample 101 may be supported by a stage configured to actuate the sample 101 to a selected position (i.e. placing a defect of interest into view). For example, the stage may be mechanically coupled to or include one or more motors, servos, or alternative actuation means configured to spin the sample 101 about its central axis to place a selected portion of the sample edge 102 into view.

The system 100 further includes at least one line scan detector 108, such as a polychrome or monochrome line scan camera (e.g. CCD or CMOS linear sensor array). The line scan detector 108 is configured to receive at least a portion of illumination reflected from the sample edge 102 along a collection path defined by one or more collection optics 110. This line scan camera function can also be achieved by using a 2-D sensor and windowing out a minimal number of lines. In some embodiments, the collection optics 110 include an objective lens assembly, such as a brightfield objective. A beam splitter 112 disposed between the collection optics 110 and the sample edge 102 may be configured to direct illumination from the illumination path to the sample edge 102 and direct illumination reflected from the sample edge 102 back through the collection optics 110 to the line scan detector 108. Placement below the objective 110 may enable angle of incidence variations; however, the beam splitter 112 may be alternately disposed between the line scan detector 108 and the objective 110 if angle of incidence is maintained substantially uniform while scanning the sample edge 102.

Figure 2:
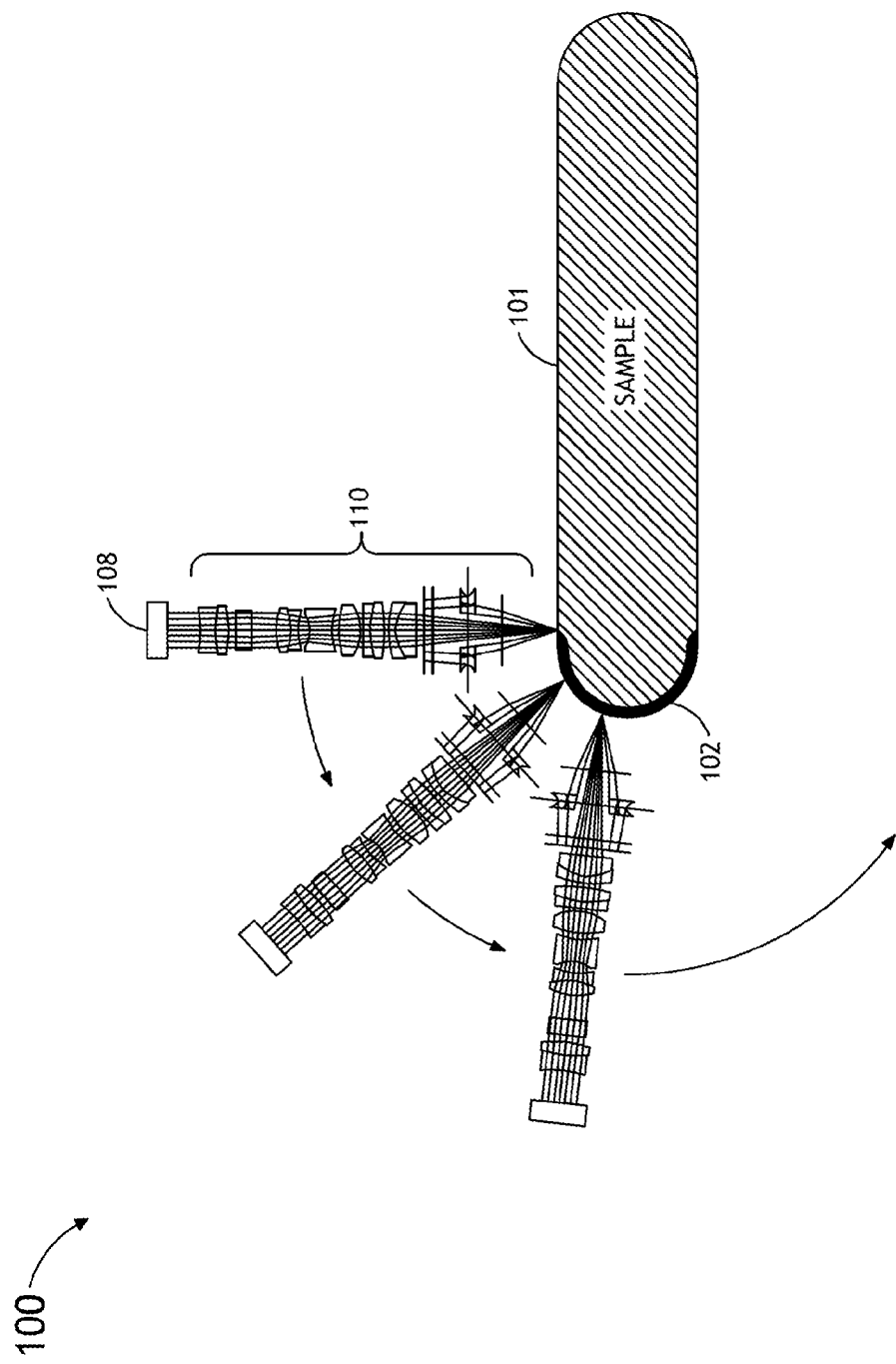
FIG. 2 illustrates a line scan detector an collection optics radially actuated about the edge of a sample, in accordance with an embodiment of this disclosure.

As illustrated in FIG. 2, the line scan detector 108 is configured to scan across at least a portion of the sample edge 102 by following an actuation path defined by the edge profile. One or more actuators are mechanically coupled to at least the line scan detector 108 and the collection optics 110. In some embodiments, the line scan detector 108 and the collection optics 110 are supported by a stage coupled to the one or more actuators. The one or more actuators are configured to radially actuate the line scan detector 108 and the collection optics 110 along the actuation path (over and under a portion of the sample 101) to enable scanning across the selected portion of the sample edge 102.

The one or more actuators may be configured to translate and/or rotate the line scan detector 108 and the collection optics 110 along at least three axis (or six degrees of freedom) to enable control of focus and angle of incidence. In some embodiments, the illumination source 104 and illumination optics 106 are also coupled to the one or more actuators for scanning convenience. For example, the illumination source 104 and optics 106 may be disposed upon the stage supporting the line scan detector 108 and the collection optics 100 to enable simultaneous actuation. In some embodiments, a plurality of actuators (e.g. motors/servos) may operate in concert to follow the edge profile while maintaining a substantially uniform level of focus and angle of incidence (e.g. substantially normal incidence). Accordingly, the line scan detector 108 may be enabled to collect high resolution (e.g. 3 to 5 um pixel resolution) review images of the scanned portion of the sample edge 102.

In some embodiments, the system 100 further includes a second illumination source 120 configured to provide illumination along a second illumination path to illuminate the sample edge 102. A beam splitter 122 may be configured to merge a first illumination path corresponding the first illumination source 104 and the second illumination path corresponding the second illumination source 120 into a common illumination path leading to the sample edge 102. Each channel may be configured for imaging the sample edge 102 according to a different review protocol. For example, the first illumination source 104 may be configured to illuminate the sample edge 102 to collect brightfield review images, and the second illumination source 120 may be configured to illuminate the sample edge 102 to collect darkfield review images. In either mode of operation, the same collection optics 110 (e.g. a brightfield objective) may be configured to direct illumination reflected from the sample edge 102 to the line scan detector 108. Accordingly, the line scan detector 108 may be configured to collect brightfield or darkfield review images of the sample edge 102 depending upon the illumination source 104 or 120 illuminating the sample edge 102 during a scan.

At least one computing system 114 communicatively coupled to line scan detector 108 is configured to process data collected from a plurality of scanned locations along the sample edge 102. For example, the computing system 114 may be configured to generate a review image of at least a portion of the sample edge 102 by merging multiple line scans. In some embodiments, the computing system 114 may include at least one processor (e.g. single-core or multiple-core processor) configured to execute program instructions 118 from at least one carrier medium 116, wherein the program instructions 118 direct the processor to carry out one or more of the steps or functions described herein. The one or more computing systems 114 may be further configured to control the one or more actuators of the sample stage or the illumination/collection optics to scan a selected portion of the sample edge 102, as described above.

In some embodiments, the one or more computing systems 114 are further configured to control illuminations source 104 and/or 120 to provide pulses of illumination to for illumination uniformity and/or focus as the sample edge 102 is scanned. For example, each illumination source 104/120 may include at least one light emitting diode (LED) configured to strobe illumination to compensate for variations in illumination intensity that can occur between scanning locations as a result of non-uniform motion along the actuation path.

Figure 3:
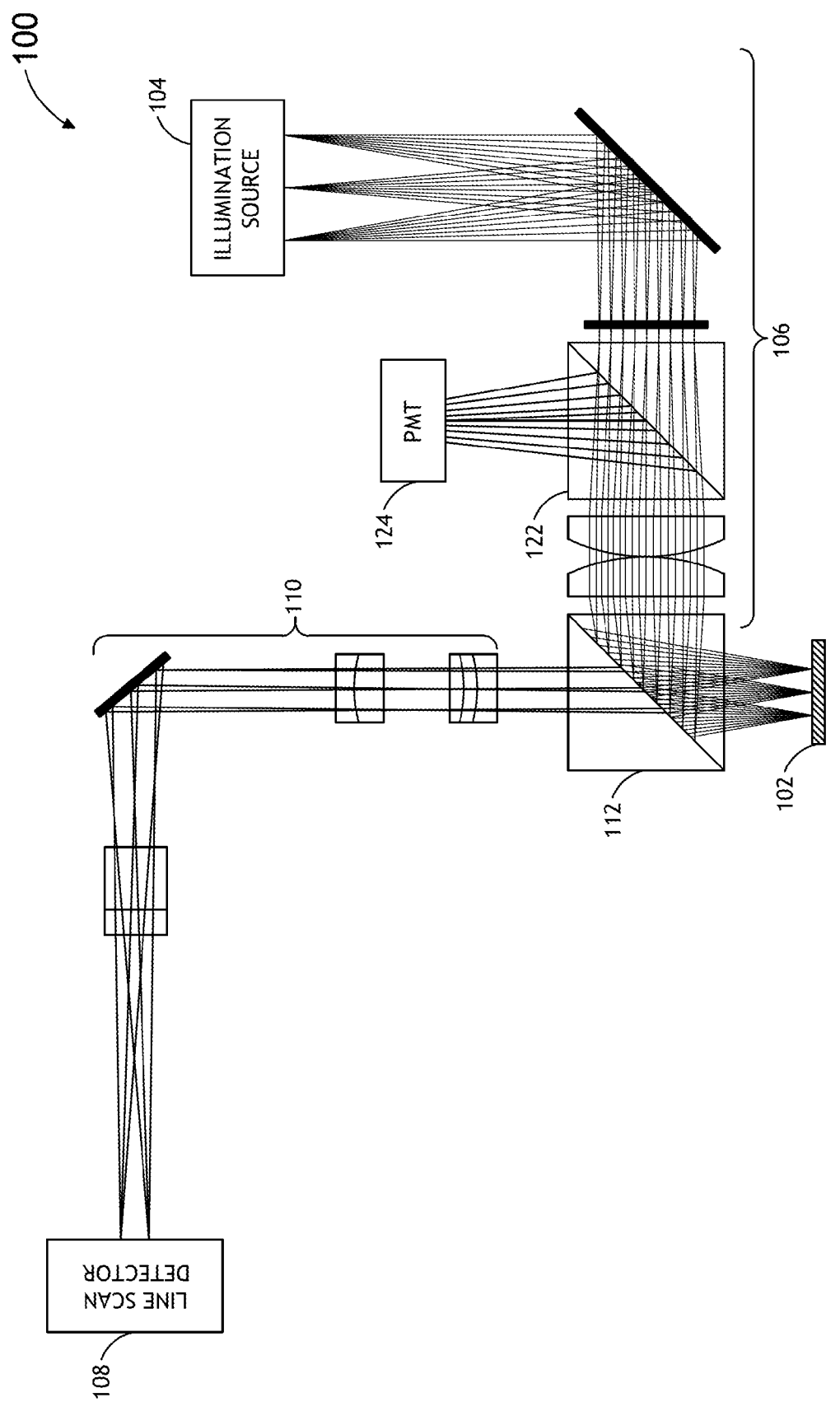
FIG. 3 is a block diagram illustrating a system for reviewing an edge of a sample, further including a photomultiplier tube for inspecting the edge of the sample, in accordance with an embodiment of this disclosure.

FIG. 3 illustrates another embodiment of the system 100 including a scatter channel photomultiplier tube 124 to enable inspection in addition to review of the sample edge 102. In some embodiments, the photomultiplier tube 124 is disposed in place of the second illumination source 120 (from FIG. 1), wherein the beam splitter 122 is configured to direct at least a portion of illumination reflected or scattered from the sample edge 102 along a scatter channel to the photomultiplier tube 124. Alternatively, the scatter channel is incorporated in addition to the first and second illumination channels utilizing an additional beam splitter in series with the first beam splitter 122. The one or more computing systems 108 may be further coupled to the photomultiplier tube 124 and configured to determine location, size, and/or classification of at least one defect of the sample 101 utilizing information associated with illumination received by the photomultiplier tube 124.

Figure 4:
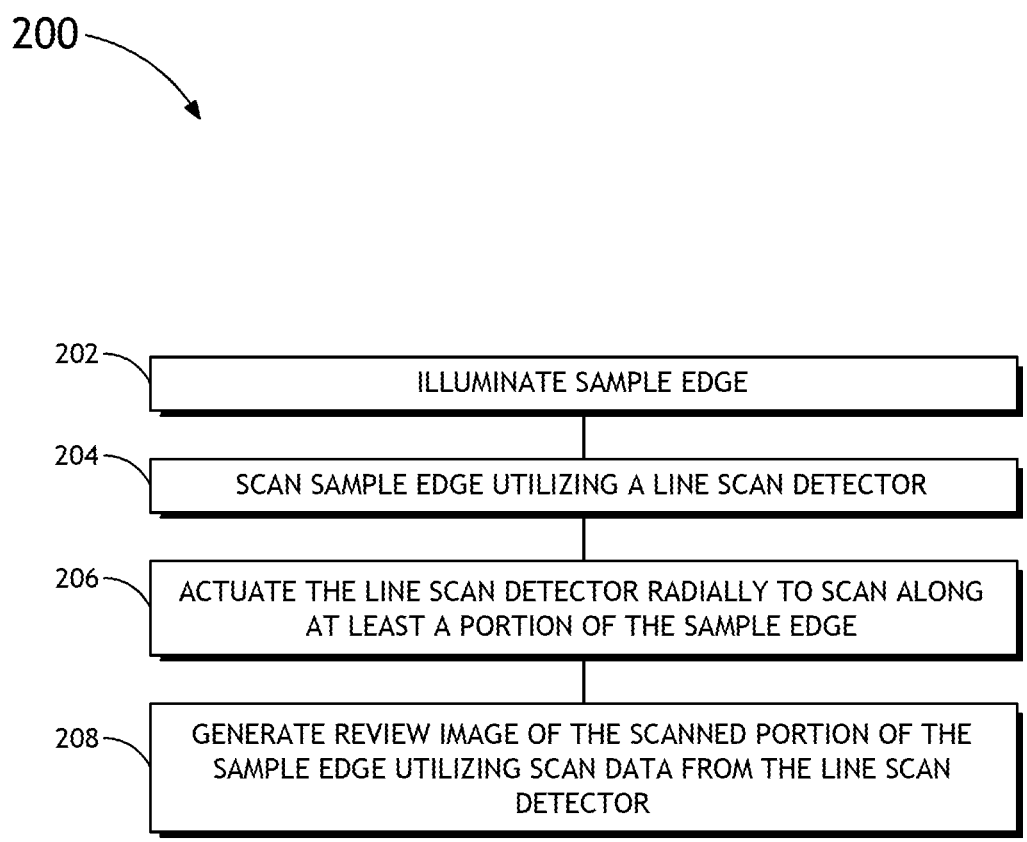
FIG. 4 is a flow diagram illustrating method of reviewing an edge of a sample, in accordance with an embodiment of this disclosure.

FIG. 4 illustrates a method 200 of reviewing a sample edge 102 in accordance with the foregoing system 100. It is noted, however, that method 200 may be implemented by alternative or additional means known to the art than those described by the foregoing embodiments of system 100. Accordingly, method 200 should be construed as encompassing any means known now or hereafter for executing one or more of the following steps or functions. Furthermore, method 200 is not limited to the following steps and may include one or more steps for carrying out any of the functions described above with regard to embodiments of system 100.

At step 202, an edge 102 of a sample 101 is illuminated utilizing at least one illumination source 104 and/or 120. In some embodiments, pulsed illumination is utilized to enable focusing and/or compensation for non-uniform actuation about the sample edge 102. At steps 204 and 206, a plurality of line scans are detected by actuating a line scan detector 108 along an actuation path defined by the sample edge 102. In some embodiments, the scans are collected while maintaining a substantially normal angle of incidence with the scanned portion of the sample surface. At step 208, the scan data (i.e. 1-D line scans) are assembled into a (2-D) review image of at least a portion of the sample edge 102. Accordingly, a high resolution image of the sample edge 102 is collected by following the edge profile to scan over a plurality of locations along the sample edge.

The foregoing system 100 and method 200 provide several advantages over the current art. By scanning over the edge of the wafer with a line array, the angle of incidence to the wafer over a 4 mm wide swath, for example (consistent with a 0.125 NA, 1 um pixel resolution) would only be 0.0089 radians, which is a very small fraction of the basic NA. Shading in a thru the lens illumination would be ~8% (compared to 100% darkening for the alternate methods at only 2% of this field of view. Addition of under-the-lens illumination allows a slight overfilling of the objective NA, and allows minor misalignment and local surface tilt without any illumination vignetting. Adding a scatter channel option through the same beam splitter path allows for convenience of stage motion for inspection and review. The advantages can be further extended to applications beyond edge review images. For example, the system 100 and method 200 described above can be further configured for inspecting a film disposed upon a wafer at an angle, with the angle of incidence in radial slice planes.

It should be recognized that the various steps and functions described throughout the present disclosure may be carried out by a single computing system or by multiple computing systems. The one or more computing systems may include, but are not limited to, a personal computing system, mainframe computing system, workstation, image computer, parallel processor, or any other device known in the art. In general, the term "computing system" may be broadly defined to encompass any device having one or more processors, which execute instructions from at least one carrier medium.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for reviewing a curved edge of a sample, comprising:
   a stage configured to support a sample;
   at least one illumination source configured to illuminate an edge of the sample with illumination emanating from the at least one illumination source along an illumination path including one or more illumination optics;
   a line scan detector configured to receive illumination reflected from the edge of the sample along a collection path including one or more collection optics;
   at least one actuator mechanically coupled to the line scan detector and the one or more collection optics, the at least one actuator configured to simultaneously actuate the line scan detector and the one or more collection optics around the edge of the sample along a radial direction, wherein the line scan detector is configured to acquire multiple line scans along an actuation path of the at least one actuator, and wherein the illumination source is configured to compensate for non-uniform actuation by the at least one actuator; and
   a computing system communicatively coupled to the line scan detector, the computing system configured to generate at least one review image of at least a portion of the edge of the sample utilizing scan data associated with illumination received by the line scan detector from a plurality of locations along the edge of the sample, wherein the at least one review image is generated at least by merging two or more of the multiple radial line scans.

2. The system of claim 1, wherein the line scan detector includes at least one CCD or CMOS linear sensor array.

3. The system of claim 1, wherein the line scan detector includes at least one polychrome or monochrome line scan camera.

4. The system of claim 1, wherein the line scan detector comprises a two dimensional camera.

5. The system of claim 4, wherein the two dimensional camera is configured to approximate a line scan camera by windowing out a minimal number of lines.

6. The system of claim 1, wherein the at least one actuator is further coupled to the at least one illumination source and the one or more illumination optics, and wherein the at least one actuator is further configured to actuate the at least one illumination source and the one or more illumination optics radially along the actuation path defined by the edge of the sample.

7. The system of claim 6, wherein the at least one actuator is configured to maintain a substantially normal angle of incidence between the one or more illumination optics and the edge of the sample.

8. The system of claim 6, wherein the at least one illumination source includes at least one light emitting diode configured to strobe illumination to compensate for non-uniform actuation by the least one actuator.

9. The system of claim 1, further comprising:
a photomultiplier tube configured to receive illumination reflected or scattered from the edge of the sample along a second collection path, wherein the computing system is further configured to determine a location of at least one defect of the sample utilizing information associated with illumination received by the photomultiplier tube.

10. The system of claim 1, wherein the one or more illumination optics include an oversized numerical aperture configured to compensate for errors in alignment while maintaining illumination fill of an objective collection pupil of the one or more collection optics.

11. A system for reviewing a curved edge of a sample, comprising:
a stage configured to support a sample;
a first illumination source configured to illuminate an edge of the sample with illumination emanating from the first illumination source along a first illumination path including one or more illumination optics;
a second illumination source configured to illuminate the edge of the sample with illumination emanating from the second illumination source along a second illumination path including one or more illumination optics;
a line scan detector configured to receive illumination reflected from the edge of the sample along a collection path including one or more collection optics;
at least one actuator mechanically coupled to the line scan detector and the one or more collection optics, the at least one actuator configured to simultaneously actuate the line scan detector and the one or more collection optics around the edge of the sample along a radial direction, following an actuation path defined by the actuator, and wherein at least one of the first and second illumination sources is configured to compensate for non-uniform actuation by the least one actuator; and
a computing system communicatively coupled to the line scan detector, the computing system configured to generate at least one review image of at least a portion of the edge of the sample utilizing scan data associated with illumination received by the line scan detector from a plurality of locations along and around the edge of the sample, wherein the at least one review image is generated at least by merging the multiple radial line scans.

12. The system of claim 11, wherein the line scan detector includes at least one CCD or CMOS linear sensor array.

13. The system of claim 11, wherein the line scan detector includes at least one polychrome or monochrome line scan camera.

14. The system of claim 11, wherein the line scan detector comprises a two dimensional camera.

15. The system of claim 14, wherein the two dimensional camera is configured to approximate a line scan camera by windowing out a minimal number of lines.

16. The system of claim 11, wherein the first illumination source is configured to illuminate the edge of the sample for brightfield imaging, and the second illumination source is configured to illuminate the edge of the sample for darkfield imaging.

17. The system of claim 11, further comprising:
a beam splitter configured to merge the first illumination path and the second illumination path into a common illumination path leading to the edge of the sample.

18. The system of claim 11, wherein the at least one actuator is further coupled to each of the first and second illumination sources and the respective illumination optics of the first and second illumination paths, and wherein the at least one actuator is further configured to actuate the each of the first and second illumination sources and the respective illumination optics of the first and second illumination paths radially along the actuation path defined by the edge of the sample.

19. The system of claim 18, wherein the at least one actuator is configured to maintain a substantially normal angle of incidence between the respective illumination optics of the first and second illumination paths and the edge of the sample.

20. The system of claim 18, wherein at least one of the first and second illumination sources includes at least one light emitting diode configured to strobe illumination to compensate for non-uniform actuation by the least one actuator.

21. The system of claim 11, further comprising:
a photomultiplier tube configured to receive illumination reflected or scattered from the edge of the sample along a second collection path, wherein the computing system is further configured to determine a location of at least one defect of the sample utilizing information associated with illumination received by the photomultiplier tube.

22. The system of claim 11, wherein the one or more illumination optics include an oversized numerical aperture configured to compensate for errors in alignment while maintaining illumination fill of an objective collection pupil of the one or more collection optics.

23. A method of reviewing a curved edge of a sample, comprising:
illuminating an edge of a sample with illumination emanating from a first illumination source along a first illumination path including one or more illumination optics;
receiving illumination reflected from the edge of the sample along a collection path including one or more collection optics utilizing a line scan detector;
actuating simultaneously the line scan detector, the first illumination source, and the one or more collection optics around the edge of the sample along a radial direction, following an actuation path defined by the edge of the sample;
using the first illumination source to compensate for non-uniform actuation; and
generating at least one review image of at least a portion of the edge of the sample utilizing scan data associated with illumination received by the line scan detector acquiring multiple radial line scans from a plurality of locations along the actuation path around the edge of the sample, wherein the at least one review image is generated at least by merging the multiple radial line scans.

24. The method of claim 23, further comprising:
illuminating the edge of the sample with illumination emanating from a second illumination source along a second illumination path including one or more illumination optics.

25. The method of claim 24, wherein the first illumination source is configured to illuminate the edge of the sample for brightfield imaging, and the second illumination source is configured to illuminate the edge of the sample for darkfield imaging.

26. The method of claim 23, further comprising:
merging the first illumination path and the second illumination path into a common illumination path leading to the edge of the sample utilizing a beam splitter.

27. The method of claim 23, further comprising:
actuating the first illumination sources and the one or more illumination optics of the first path radially along the actuation path defined by the edge of the sample.

28. The method of claim 27, further comprising:
maintaining a substantially normal angle of incidence between the one or more illumination optics of the first illumination path and the edge of the sample.

29. The method of claim 27, further comprising:
strobing illumination emanating from the first illumination source to compensate for non-uniform actuation.

30. The method of claim 23, further comprising:
receiving illumination reflected or scattered from the edge of the sample along a second collection path utilizing a photomultiplier tube; and
determining a location of at least one defect of the sample utilizing information associated with illumination received by the photomultiplier tube.

31. The method of claim 23, wherein the one or more illumination optics include an oversized numerical aperture configured to compensate for errors in alignment while maintaining illumination fill of an objective collection pupil of the one or more collection optics.

* * * * *